United States Patent [19]

Toth

[11] 4,365,198
[45] Dec. 21, 1982

[54] METHOD AND APPARATUS FOR DETECTING, CLASSIFYING AND MARKING DEFECTS IN WORKPIECE WITH IMPROVED TIMING CONTROL

[75] Inventor: James M. Toth, Lyndhurst, Ohio

[73] Assignee: Republic Steel Corporation, Cleveland, Ohio

[21] Appl. No.: 127,579

[22] Filed: Mar. 6, 1980

[51] Int. Cl.³ .................... G01N 27/72; G01R 33/00
[52] U.S. Cl. .................................... 324/226; 324/262
[58] Field of Search ................ 324/225, 226, 234-243

[56] References Cited

U.S. PATENT DOCUMENTS

| | | |
|---|---|---|
| 2,660,704 | 11/1953 | Harmon . |
| 2,832,040 | 4/1958 | Harmon . |
| 2,914,726 | 11/1959 | Harmon . |
| 3,180,230 | 4/1965 | Judd et al. . |
| 3,263,809 | 8/1966 | Mandula, Jr. et al. . |
| 3,469,182 | 9/1969 | Wycherley et al. . |
| 3,486,616 | 12/1969 | Brany et al. . |
| 3,568,485 | 3/1971 | Mandula, Jr. . |
| 3,617,875 | 11/1971 | Mandula, Jr. et al. . |
| 3,673,493 | 6/1972 | Hoffman et al. ........... 324/226 |
| 3,675,118 | 7/1972 | Booth ........................ 324/226 |
| 4,082,182 | 4/1978 | Grimell et al. . |

Primary Examiner—Gerard R. Strecker
Assistant Examiner—Walter E. Snow
Attorney, Agent, or Firm—Watts, Hoffmann, Fisher & Heinke Co.

[57] ABSTRACT

A workpiece 18 classifying and marking system 10 is disclosed. The system includes a probe 12 for generating signals in response to the detection of defects along the workpiece length as that workpiece rotates and traverses past the probe 12. Circuitry coupled to the test head analyzes defects according to severity and classifies the workpiece as either "good", "salvageable", or "scrap". The circuitry also causes a marker 14 to affix a flaw indicating mark to the workpiece at the flaw location.

The circuitry includes a flaw detection circuit 60, a defect classifying circuit 72, a timing control circuit 70, and a marker delay circuit 74. The timing control 70 transmits timing signals of different frequency to the defect classifying 72 and marker control 74 circuits and coordinates their operation. The defect classify circuit 72 divides the workpiece into quadrants and can sense the length of any flaws in each quadrant as the workpiece passes the probe 12. The detection of a flaw causes the timing control circuit to resynchronize itself by centering the flaw within a workpiece quadrant thereby preventing the flaw from "wandering" out of the quadrant. The circuitry is controllable by the user to change workpiece classification as a function of the use to which the workpiece is to be put.

3 Claims, 7 Drawing Figures

METHOD AND APPARATUS FOR DETECTING, CLASSIFYING AND MARKING DEFECTS IN WORKPIECE WITH IMPROVED TIMING CONTROL

DESCRIPTION

1. Technical Field

This invention relates to flaw inspection in work pieces and more specifically to circuitry for controlling marking and classification of flaws in steel billets or bars.

2. Background Art

Work piece flaw detection and classification systems are known. The Republic Steel Corporation has developed a number of innovative flaw detecting systems and a number of patents have issued describing these systems.

One of the earlier Republic Steel flaw detecting patents is U.S. Pat. No. 2,660,704 to Harmon. That patent discloses a test device for locating flaws such as cracks, seams, breaks, and the like in a steel workpiece by measurements conducted at the surface of the workpiece. The apparatus disclosed in the '704 patent includes a search unit adapted to be positioned upon or adjacent a workpiece and for subjecting the workpiece to a periodically varying electro-magnetic field produced by a coil carried in the search unit. Suitable control and flaw indication circuitry is coupled to the search unit to convert signal variations produced by movement of the search unit about the workpiece circumference into an indication as to the relative characteristics of the various portions of the bar. U.S. Pat. Nos. 2,914,726 and 2,832,040 disclose improvements and refinements in the technique disclosed in the '704 patent.

Two more recent Republic Steel patents disclose control circuitry and apparatus for utilizing the detecting principle disclosed in the '704 patent to classify and mark the position of defects in steel bars as they are tested. These two patents are U.S. Pat. Nos. 3,108,230 to Judd et al and 3,263,809 to Mandula et al. Both patents are used in conjunction with a test probe which is moved relative to a steel bar and coupled to energization circuitry for generating electromagnetic signals within the bar.

According to the '809 patent, the defect information obtained by the probe or test head is acted upon by a detection circuit which produces an output voltage pulse in response to the presence of a defect. The pulse amplitude is related to the depth of the defect and is introduced to a classifier circuit having two channels. One channel generates a trigger signal each time a relatively deep defect is sensed and a second channel generates a trigger pulse each time either a shallow or a deep defect has been sensed. These trigger pulses are introduced into an analyzer section which counts the number of shallow and deep defect trigger pulses for a given area of the workpiece, and from this information determines the severity of the combinations of defects. The analyzer section then classifies the workpiece or bar according to the combined severity as either good, salvage, or scrap.

As the name suggests, "good" workpieces are those which have no defects, or defects which are not objectionable since they do not impair the utility of the product for its intended purpose. Workpieces classified as "salvage" have defects deep enough to be objectionable but not too severe to preclude repair. A "scrap" workpiece is one in which the defects are so deep and so long that it is not possible to salvage the workpiece.

The '230 patent discloses defect marking apparatus which marks the location of the defects on the workpiece. The marks made are permanent and easily visible even though the workpiece may be subject to abrasive handling. The '230 patent discloses a rotating cutter of carbide or other material which is movable to engage the workpiece and cut impressions therein at defect locations. An actuator is adapted to move the cutter onto the workpiece for the duration of an energizing pulse. Actuation is coordinated with defect detection equipment constructed, for example, in accordance with the earlier Harmon patent. The detection equipment and workpiece are relatively rotatable such that the detection equipment describes a helical path around a longitudinally moving workpiece. The control circuit is connected to both the detection equipment and to the actuator on the defect marking equipment and causes an energizing signal to activate the actuator to effect appropriate defect marking.

Since the cutter or marking system and the defect detection equipment cannot be at the same physical location, the marker is placed behind or "downstream" of the detection equipment. Both are preferably placed on a longitudinal line along the bar. The longitudinal space between the marker and the detection equipment is chosen to equal the distance of travel per revolution of workpiece movement. Upon receipt of a defect signal from the detection equipment, the control circuit coupled to the marker system delays sending an energization signal for a period of time equal to one bar revolution. Since forward bar travel per revolution is equal to the spacing between the detection equipment and the marker, the energization signal causes the mark to be applied to the bar at the location of the detected defect.

The concepts embodied in the Mandula et al and Judd et al patents enable bars to be marked and classified in a unified system which has proven to be very effective. The control circuitry utilized, however, for coordinating bar marking and classification is an analog electronic circuit which is not always sensitive to closely spaced multiple defects. The prior classification and marking system can only classify seams or cracks once every revolution of a bar or workpiece. If a plurality of deep seams exist about the circumference of the bar, the Mandula et al system analyzes only the first such defect and ignores subsequently sensed defects. This lack of sensitivity in defect sensing can result in errors in bar classification. If a short deep defect is first sensed along the path of workpiece travel, an accompanying long deep defect may not be properly measured and therefore a workpiece classified as good may in reality be either a salvage or scrap bar.

The prior art classification and marking system includes a plurality of separate analog timing circuits for controlling and coordinating classification and marking. Both the deep and shallow flaw measuring channels in the classification circuit each has its own timing mechanism which resets the classification circuitry in its associated channel after each bar revolution. In addition to these two timing circuits a third timing circuit is required to delay the marking of flaw position on the workpiece. Typically, more than one marker is positioned along the workpiece and these multiple markers each require a separate timer. As bars of different physical dimensions are examined, each of the multiple timers must be adjusted by the system operator.

In the prior art classifying process an attempt was made to resynchronize the multiple timing control circuits in response to the presence of flaws along the bar. The resynchronization circuitry was analog electronics, however, and was subject to drift in operating characteristics with temperature. Synchronization between the timing circuitry and bar rotation could be lost with possible inaccurate bar classification as well as inaccurate marking of flaw location.

Thus, although the prior art techniques for marking and classifying steel bars were effective, they exhibited shortcomings. In particular, the resynchronization and timing procedures utilized in the prior art classifying system were somewhat ineffective. In addition to these disadvantages, the prior art analog circuitry was weighty, consumed a moderate amount of power and was subject to drift in operating characteristics with temperature.

DISCLOSURE OF INVENTION

The present invention overcomes disadvantages noted with regard to the prior art by using a single timing circuit to synchronize the classification and marking of defects along the length of a workpiece. With a single timing circuit only a single adjustment need be made for workpieces of different diameters.

The invention includes a detector and detector circuitry for sensing defects in a workpiece as the workpiece moves past a detector and for generating an output having a level related to the severity of a detected defect. The detector circuitry is coupled to a defect classifying circuit which classifies the workpiece according to defect severity. The defect detector circuitry is also coupled to workpiece marking control circuitry for receiving defect signals and causing the position of the defects to be marked on the workpiece. A single timing circuit coupled to both the defect classifying circuit and the workpiece marking circuit controls the operation of those circuits.

According to a preferred embodiment of the invention, the defect classifying and marking circuits each include a storage circuit for storing defect signals received from the detector. In the marking circuit, the storage circuit provides a convenient technique for delaying activation of a marker until the workpiece rotates one complete revolution after a defect is sensed. A signal from the detection circuit is stored in the marker circuit an appropriate time as dictated by clocking pulses from the timing circuit and then signals a marker activation circuit. During this time the workpiece continues to rotate and traverse past the detector so that when the marker is activated the sensed defect is adjacent the marker.

The defect classification circuit storage circuit stores subsequent ones of defect signals from the detection circuit and provides a technique for classifying the defect according to length. The classifying storage circuit includes a gating input for transmitting defect signals through the classifying storage circuit at a rate related to workpiece speed of rotation and generated by the single timing circuit.

According to the preferred embodiment of the invention the classifying circuit storage portion comprises a serial shift register. Storage locations in the shift register are sampled by logic circuitry to determine the number of consecutive rotations of a bar being inspected which produced signals indicating the presence of a particular defect and thereby determine the length of that defect. The timing control circuit clocks the shift register four times for every workpiece revolution. If a defect signal is stored every fourth shift register location for a significant portion of shift register memory it is known a long seam has been sensed. By knowledge of the speed of workpiece travel past the detector the length of this seam is known.

Clocking the shift register at a rate four times greater than workpiece rotation divides the workpiece into four quadrents for defect classification. By dividing the workpiece into quadrants the circuitry provides a degree of sensitivity unavailable in the prior art. Two distinct defects occurring along the workpiece but in separate ones of the quadrants will each be analyzed and categorized according to length by the improved control circuitry.

The timing circuitry employed in the preferred embodiment of the invention comprises a signal generator for generating two separate series of pulses. Each of these series is coordinated with the workpiece revolution. A first one of the series is coupled to the bar marking control circuitry and serves as a gating signal to the marker storage circuit discussed previously. The second of the two series of pulses is the signal with a repetition frequency four times greater than the period of bar revolution for gating the classifying circuit serial shift register.

The timing circuit resynchronizes pulses in this second series upon the detection of a workpiece defect. According to the preferred timing circuit, the detection of a defect along the length of the bar causes the next clocking pulse in the second series to occur one eighth bar revolution later in time. Once a defect is sensed, this resynchronization centers the defect in the middle of a particular workpiece quandrant as defined by the second series of pulses. According to this scheme, variations in workpiece speed of rotation unless drastic, will not allow a particular flaw to "wander" out of its particular quandrant. The resulting resynchronization thereby results in a more accurate and more sensitive flaw classification circuit.

The preferred marker delay, classification and timing circuits are digital. Digital circuitry is lighter, more reliable and consumes less power than the prior art analog control. It can be packaged in a smaller package and generally performs its control functions more reliably.

It should be apparent from the above that one object and aspect of the present invention is an increase in classifying circuit sensitivity and reliability to increase the accuracy of the classification technique. A second object of the invention is to provide a unified and simple timing circuit to control both classification and marking. A third object and feature is to resynchronize the classification circuitry each time a defect is sensed to insure that variations in the mechanical rotation of the bar do not introduce inaccuracies into the classification process. Other objects and features of the present invention will be understood more clearly when the present invention is considered in conjunction with the drawings and their description which follows.

BEST MODE FOR CARRYING OUT THE INVENTION

Figure 1:
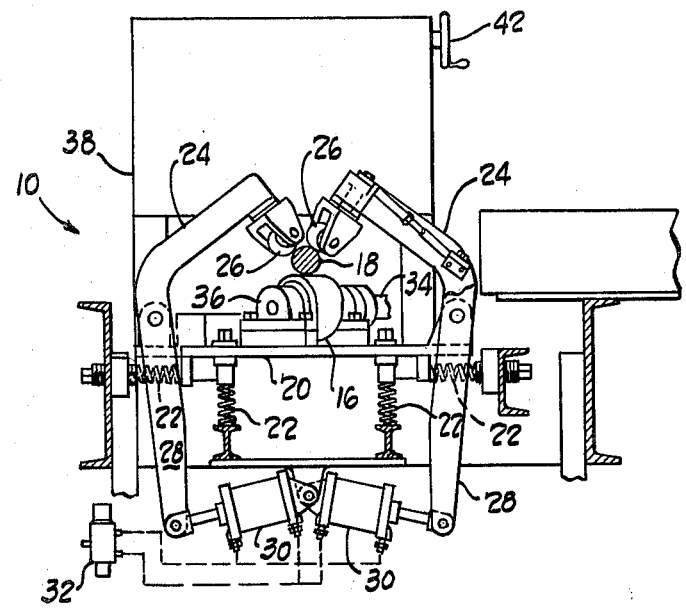
FIG. 1 is a front elevational view of a workpiece inspection station.
Figure 2:
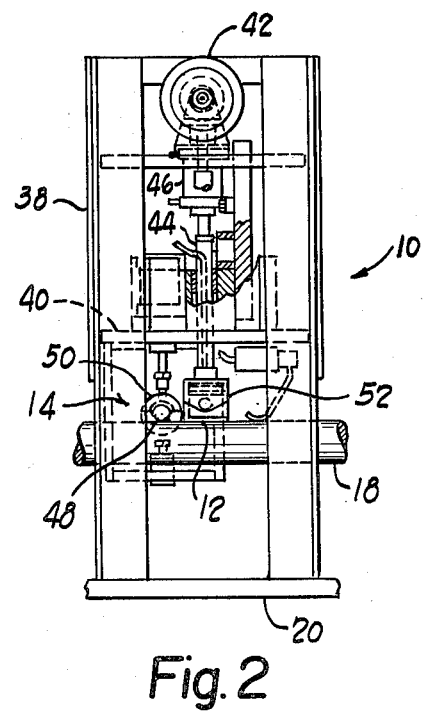
FIG. 2 is a side elevation view of the inspection station as shown in FIG. 1.

Referring now to the drawings, FIGS. 1 and 2 show a workpiece inspection station 10 where a flaw detection probe 12, marker 14 and drive roller 16 are shown in proximity to a workpiece 18. The probe 12 is coupled to analysis circuitry to be described which controls the marker 14 and also controls classification of the workpiece under examination. The drive roller 16 provides relative movement between the probe 12 and the workpiece 18.

As seen in FIG. 1, the roller 16 is supported by a float plate 20 carried on both horizontal and vertical springs 22. A pair of hold down arms 24 with swiveled rollers 26 are carried by the float plate 20 above the drive roller 16. The hold down arms 24 include lever arm extensions 28 which are pivoted by piston rods of two cylinders 30. The cylinders are actuated by a control valve 32 causing the hold down arms 24 to bias the workpiece 18 in contact with the drive roller 16.

The roller 16 which supports the workpiece 18 is carried by a shaft 34 which is rotatably journaled in a pillow block 36. The shaft 34 includes an extended shaft portion which extends beyond the pillow block for driving connection to a suitable motor for providing rotation of the shaft and accompanying drive roller 16. The axes of rotation of the roller and accompanying shaft are set at an angle with respect to the line of travel of the workpiece. Rotation of the drive roller 16 causes longitudinal movement of the workpiece 18 in a direction perpendicular to FIG. 1 as well as rotation about an axis co-incident with the workpiece center.

Referring now to FIG. 2 an inspection and marking assembly support frame 38 is positioned behind the drive roller 16 and mounted to the float plate 20. The frame 38 supports a probe and marker carriage 40 which is slidably carried by the frame 38. The vertical position of the probe and marker carriage 40 can be adjusted by rotating a hand crank 42 which allows different size workpieces to be scanned. The probe 12 is carried by a probe positioning shaft 44 which is attached to a piston rod of a probe positioning cylinder 46. A solenoid actuated control valve (not shown) is pneumatically coupled to the cylinder 46 and controls actuation of that cylinder to extend and retract its piston rod to position the probe 12 against the workpiece 18.

The marker 14 is also carried by the inspection marking support frame 38. The marker comprises a carbide cutter 48 which is fixed to a shaft of a motor 50. A spring (not shown) biases the cutter 48 in spaced relation out of engagement with the workpiece 18. A cylinder carried by the probe and marker carriage 40 has a piston rod connected to a shaft collar at a point just above the cutter and causes the cutter 48 to engage the workpiece each time the cylinder is activated by a suitable control signal such as a solenoid actuated air valve.

A gimbel assembly 52 connects the search probe 12 to the end of the probe positioning shaft 44. The gimbel assembly 52 allows the search probe 12 to move universally at the end of the positioning shaft 44 as the probe contacts the workpiece.

Although only one inspection station 10 has been shown, it should be appreciated that a plurality of such stations may be provided. For example, a number of inspection and marking assemblies may be spaced longitudinally along the path of the workpiece travel so that each inspection station inspects only a portion of the workpiece with all assemblies providing entire workpiece coverage.

The inspection station 10 shown in FIGS. 1 and 2 is an exemplary inspection station. Other configurations and designs might be used in conjunction with the present invention to detect, classify and mark a workpiece according to defect severity. Additional details of the exemplary inspection station 10 may be found in U.S. Pat. No. 3,263,809 to Mandula et al. which has been assigned to the assignee of the present invention. That patent is incorporated herein by reference.

Figure 3:
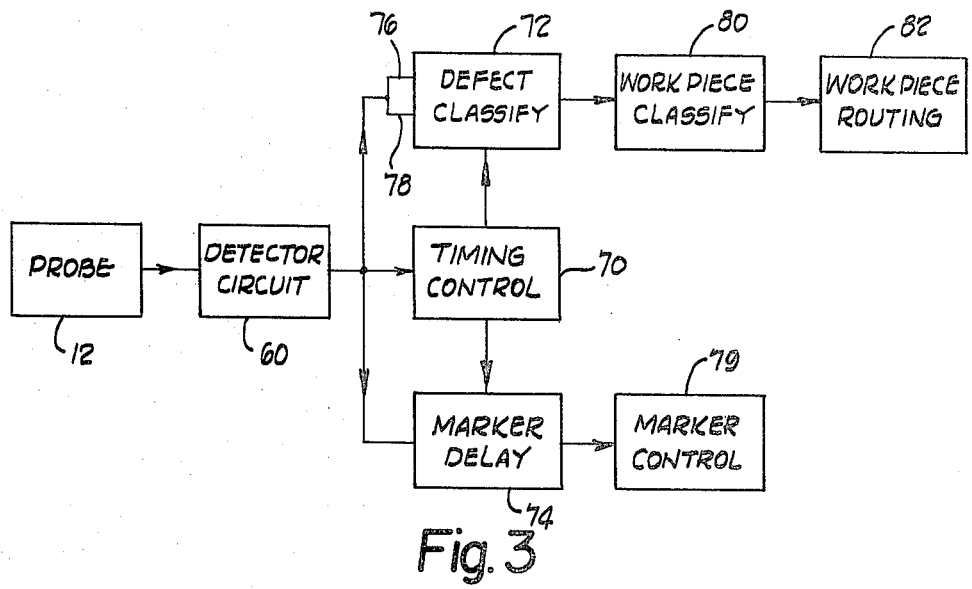
FIG. 3 shows a general schematic of control circuitry for classifying and marking the position of flaws on the workpiece

The detection probe 12 is coupled electrically to circuitry for classifying defects in the workpiece according to severity and length as well as to circuitry for marking the location of these defects on the workpiece. A schematic of the circuitry comprising the present invention is shown in FIG. 3. As seen in that Figure, the probe 12 is coupled to a detector circuit 60. The output from the detector circuit is coupled to a timing control circuit 70, a defect classifying circuit 72, and a marker delay circuit 74.

The input to the detector circuit comprises a signal related to the depth of the defect or seam in the workpiece as detected by the probe 12. Although only one detector circuit 60 is shown in FIG. 3, it should be appreciated that a plurality of such detector circuits are required if workpiece inspection is apportioned among a plurality of inspection stations.

The detector circuity 60 provides a classifying capability. It includes a threshold circuit which automatically classifies a defect as either a shallow or a severe defect and produces an output accordingly. The detector circuit 60 shown in FIG. 3 is known in the art and further details regarding such a detector circuit may be obtained by reference to the '809 patent.

As seen in FIG. 3, one timing control circuit 70 is coupled to both the defect classifying circuitry 72 and the marker delay circuitry 74. The utilization of a single timing control circuit 70 to control delay operations in the marking sequence as well as analysis operations in the defect classifying circuitry is one desirable feature of the present invention. Unlike prior art systems, one timing control circuit coordinates the marking and classification of the workpiece as that workpiece is scanned by the probe 12.

The defect classify circuit 72 includes a deep seam and shallow seam classification channel. For this reason, the connection between the detector circuit 60 and the defect classifying circuit 72 has been shown as two inputs 76, 78. One input 76 comprises an output from the detector circuit 60 from shallow seams and a second input 78 comprises detector circuit outputs from deep seams. In the exemplary embodiment of the invention the shallow seam input 76 goes "high" when a shallow seam is detected and both inputs 76, 78 go "high" when a deep seam is detected.

The defect classify circuit 72 is operative to classify both deep and shallow seams according to length. As will be described hereinafter the defect classify circuit 72 includes manually controllable switches which allow the user to choose a particular seam length as a criteria in classifying the workpiece.

Each defect, whether shallow or deep, is marked by the carbide cutter 48 under control of a marker control circuit 79. As noted above, the sequence of operations requires that a marker delay time period be introduced between the detection of a flaw by the probe 12 and the marking of that same flaw by the cutter 48. The marker delay circuit 74 achieves this function under the control of the timing control circuit 70.

Once the entire workpiece has been analyzed for seam severity and length a workpiece classify circuit 80 indicates whether the particular workpiece under study is a good, salvage, or scrap workpiece. The workpiece classify circuit 80 generates an output to a workpiece routing control circuit 82 which causes each workpiece to be routed and stored according to its classification. The functioning of the defect classify 72, timing control 70, marker delay 74, and workpiece classify 80 circuits will be described in further detail with reference to FIGS. 4-7. In those Figures the manufacturer's part numbers and pin numbers designations have been labeled on all integrated circuits to facilitate practice of the present invention.

The preferred control circuitry shown in FIGS. 4-7 analyzes signals from four probes spaced along the length of the workpiece. Each probe has an associated detection circuit 60 which generates an output signal for each deep flaw sensed as well as each shallow flaw. Since there are four probes, there are four shallow 76a, b, c, d and four deep 78a, b, c, d seam inputs to the defect classify circuit 72.

Figure 4:
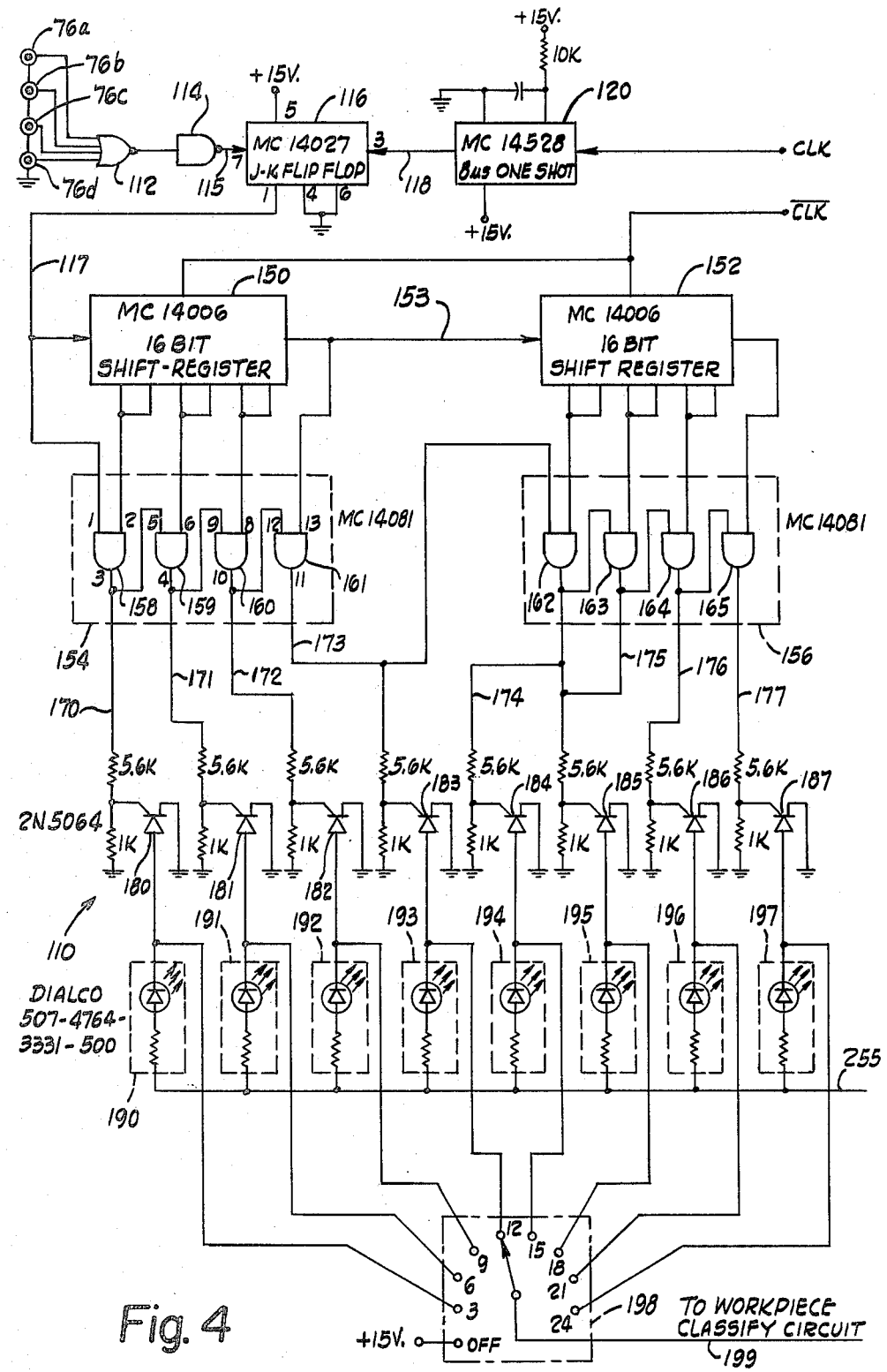

As noted above, the defect classify circuit 72 comprises a deep seam channel and a shallow seam channel. The shallow seam channel 110 is shown in FIG. 4 coupled to the four shallow seam inputs 76a, b, c, d. Circuitry identical to the circuitry shown in FIG. 4 receives the deep seam inputs and analyzes those inputs to categorize the deep seams in a manner identical to the shallow seam analysis to be described.

Each time any of the shallow seam inputs 76a, b, c, d goes high, it is an indication that an associated one of the four probes has detected a shallow seam along the workpiece length. As seen in FIG. 4, the four shallow seam inputs are coupled to a Nor gate 112. Detection of a shallow seam causes this Nor gate to generate a low output which becomes a high level output after passage through a NAND gate 114. A NAND gate output 115 is coupled to a JK flip-flop 116. This flip-flop 116 changes state in response to a high output from the NAND gate 114 unless it has already changed state in response to an earlier sensed shallow seam. The flip-flop 116 is coupled to a first 150 of two shift 16 bit registers 150, 152 via an output 117.

This flip-flop 116 is reset in response to an input 118 at pin 3 of the flip-flop from a one shot 120. The one shot in turn has an input labeled CLK from the timing control circuit 70. An input labeled $\overline{CLK}$ (not clock) from the timing control circuit 70 is a clocking input to the two shift registers 150, 152.

The 16 bit shift registers 150, 152 store shallow seam inputs 76a-d from the detection circuit 60 in response to the clock CLK and not clock $\overline{CLK}$ inputs. The appearance of a "high" shallow seam input (76 a-d) produces a "high" flip-flop output 117. The next low not clock $\overline{CLK}$ signal loads this "high" flip-flop output into the first shift register 150 at bit one. As the not clock $\overline{CLK}$ input goes low the clock input CLK goes high. After an eight microsecond delay introduced by the one shot 120 the CLK input resets the flip-flop 116 thereby preparing it fo the receipt of other shallow seam inputs 76a-d.

The timing of the clock CLK and not clock $\overline{CLK}$ inputs from the timing control circuit 70 to the one shot 120 is synchronized with rotation of the workpiece. As will become apparent four clock CLK pulses are generated for each rotation of the workpiece. Thus, four shallow seam inputs may be stored in the two shift registers per revolution of the workpiece past the probe 12. Absence of a high bit in a particular shift register means a particular workpiece quadrant contains no shallow seam or flaw.

Figure 5:
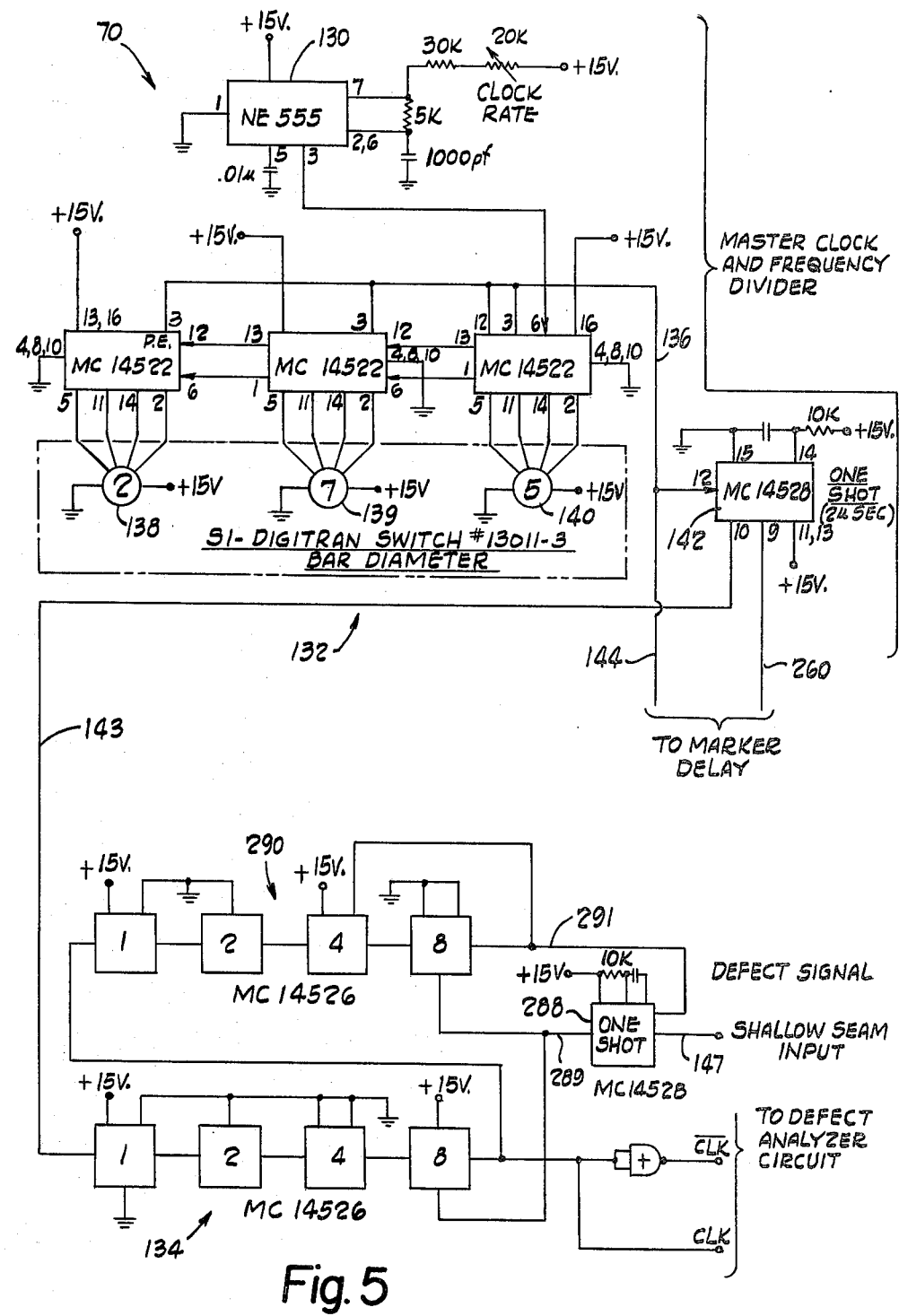

The timing control circuit is shown in FIG. 5. The clock output CLK to the one shot 120 is shown at the bottom portion of that Figure. The timing control circuitry 70 comprises an oscillator circuit 130, and a first 132 and a second 134 frequency divider circuits. The first frequency divider 132 is adjustable by the user to generate an output 136 such that the frequency of this output is related to the speed of rotation of the workpiece. In the preferred embodiment of the invention, this output is chosen to have a repetition frequency 64 times greater than the period of rotation of the workpiece.

Adjustment of the frequency along the output 136 is achieved by setting a series of three thumb-wheel switches coupled to the first frequency divider 132. The setting of the thumbwheel switches is indicated by three indicators 138-140 coupled to the thumbwheel switches. The frequency divider 132 receives the output from the oscillator 130 and divides by the number appearing on the indicators 138-140. In the setting shown in FIG. 5 the divider 132 divides the frequency of the signal output by the oscillator 130 by 275. To achieve a divider output 64 times greater than the speed of rotation of the workpiece, the user consults a table which indicates the correct thumbwheel switch settings for each size workpiece and inspection station 10 is capable of examining and dials the appropriate number into the thumbwheel switches.

The output 136 from the first frequency divider 132 is first delayed by a two microsecond one shot 142 and then transmitted to the second frequency divider 134 via an input 143. In addition to being coupled to the two microsecond one shot 142, the output 136 from the first frequency divider 132 is transmitted along an output 144 to the marker delay circuit 74. It is this output 144 which determines the clocking rate of a serial shift register 146 within the marker delay control circuit 74. (see FIG. 7).

The second frequency divider 134 divides the signal from the first frequency divider 132 by 16. This division in frequency gives a clocking signal CLK (as well as a not clock signal $\overline{CLK}$) with a clock rate four times greater than the frequency of rotation of the workpiece. From the above, it should be apparent that the timing control circuit 70 generates two outputs with differing clocking frequencies. The output 144 to the marker delay circuit has a clock frequency 64 times greater than the frequency of rotation of the workpiece and serves as a clocking pulse for the marker delay circuitry to be described hereinafter. The outputs CLK and $\overline{CLK}$ to the defect classifying circuitry 72 have a repetition rate four times greater than the frequency of rotation of the workpiece. The timing control circuit 70 in addition to generating these outputs has an input 147 which in the preferred embodiment is tied to pin No. 7 of the JK flip-flop 116 appearing in FIG. 4. It should be appreciated therefore that the input 147 goes high each time a shallow seam flaw is detected. The shallow seam input serves as a resynchronization signal to center a detected flaw within a workpiece quadrant as defined by the clocking outputs CLK and $\overline{\text{CLK}}$ from the second frequency divider. This resynchronization function will be discussed at further length after the flaw classification and workpiece classification circuits have been discussed.

Returning now to FIG. 4, the interaction between the clocking inputs from the timing control 70 and the plurality of integrated circuits comprising the shallow seam channel will be discussed. The shallow seam channel 110 comprises 2 sixteen bit registers 150, 152 and 2 Quad And gates 154, 156. A first of the 2 sixteen bit shift registers 150 includes an input coupled to the output 117 of the JK flip-flop 116. If a shallow seam is detected during the time between clock pulses from the timing circuit 70 the JK flip-flop changes states and presents a high input to the first sixteen bit shift register. Since the output 117 from the flip-flop is also tied to a first And gate 158 in the Quad And gate 154, the input on pin 1 of that And gate 158 is also high. A not clock $\overline{\text{CLK}}$ signal loads this high signal into the shift register 150 and after an 8 micro-second delay the one shot 120 resets the flip-flop 116.

As the clocking inputs (CLK and $\overline{\text{CLK}}$) continue a profile of flaw location about the workpiece is built up bit by bit in the two shift registers 150, 152. Since the clocking rate is four times greater than the speed of workpiece rotation each bit corresponds to one quadrant of workpiece coverage about the workpiece. Since the output from the first sixteen bit shift register 150 is coupled to an input 153 on the second sixteen bit shift register 152, a total of 32 quadrants or 8 revolutions of workpiece flaw information is stored in the 2 shift registers.

The two Quad And gates 154, 156 serve to monitor the condition of the bits stored in the 2 sixteen bit shift registers. The Quad And gates 154, 156 comprise 8 And gates 158-165. The first And gate 158 has one input coupled to the output 117 from the JK flip-flop 116 and a second input coupled to the fourth bit in the first sixteen bit shift register 150. When both inputs to the first And gate 158 are high, it is an indication that a shallow seam has been detected along the workpiece in the same quadrant but on two consecutive rotations of the workpiece. The speed of rotation and speed of traversal past the probe is such that this is an indication that the seam is at least three inches long. As the workpiece continues past the probe the detection circuitry continues to function and flaw indicative information is clocked through the first sixteen bit shift register until the probe again enters the quadrant in which the shallow seam was first sensed. If the same shallow flaw is present on the workpiece in the same quadrant the output from the first And gate 158 will be high and the eighth bit in the sixteen bit shift register 150 will also contain a high signal. Thus it should be apparent that input pins 5 and 6 on the second And gate 159 will also be high and therefore the output at pin 4 from the first quad And gate 154 will be high indicating that the seam is at least 6 inches long. The process continues and it should be appreciated to those skilled in the art that the combination of the series coupled sixteen bit shift registers and the two Quad And gates 154, 156 enable the circuitry to determine the length of all shallow seams on the workpiece.

The two Quad And gates have eight outputs 170-177 which are coupled to an associated one of eight thyristors 180-187. The eight thyristors are rendered conductive in response to a high output from an associated one of the And gates inside the two Quad And gate integrated circuits. A conducting thyristor causes current to pass through an associated one of eight light emitting diodes 190-197. It should be appreciated therefore that a first light emitting diode 190 will conduct and therefore emit light should a shallow seam of greater than 3 inches be detected by the probe. If the seam length is greater than 6 inches the first two light emitting diodes 190, 191 will emit light. Since there are eight light emitting diodes coupled to the eight thyristors, it is possible for those diodes to provide a visual indication of a seam length of greater than 24 inches.

The shallow channel circuit also comprises a multiposition switch 198 coupled to the anode of each of the light emitting diodes. When a particular diode is not conducting its cathode voltage is approximately 15 volts. When the LED conducts in response to a turned on thyristor, that voltage drops to approximately ½ volt. The multiposition switch 198 includes an output 199 which is coupled to one of a plurality of contacts on the multiposition switch. In the embodiment illustrated in FIG. 4, the contact is made with the LED cathode indicative of a seam length of 12 inches or greater. Once the seam length exceeds this dimension, the output 199 drops from its non-conducting 15 volt value to less than a volt. The output 199 is transmitted to the workpiece classification circuit 80 (FIG. 6) which categorizes the workpiece under study.

Figure 6:
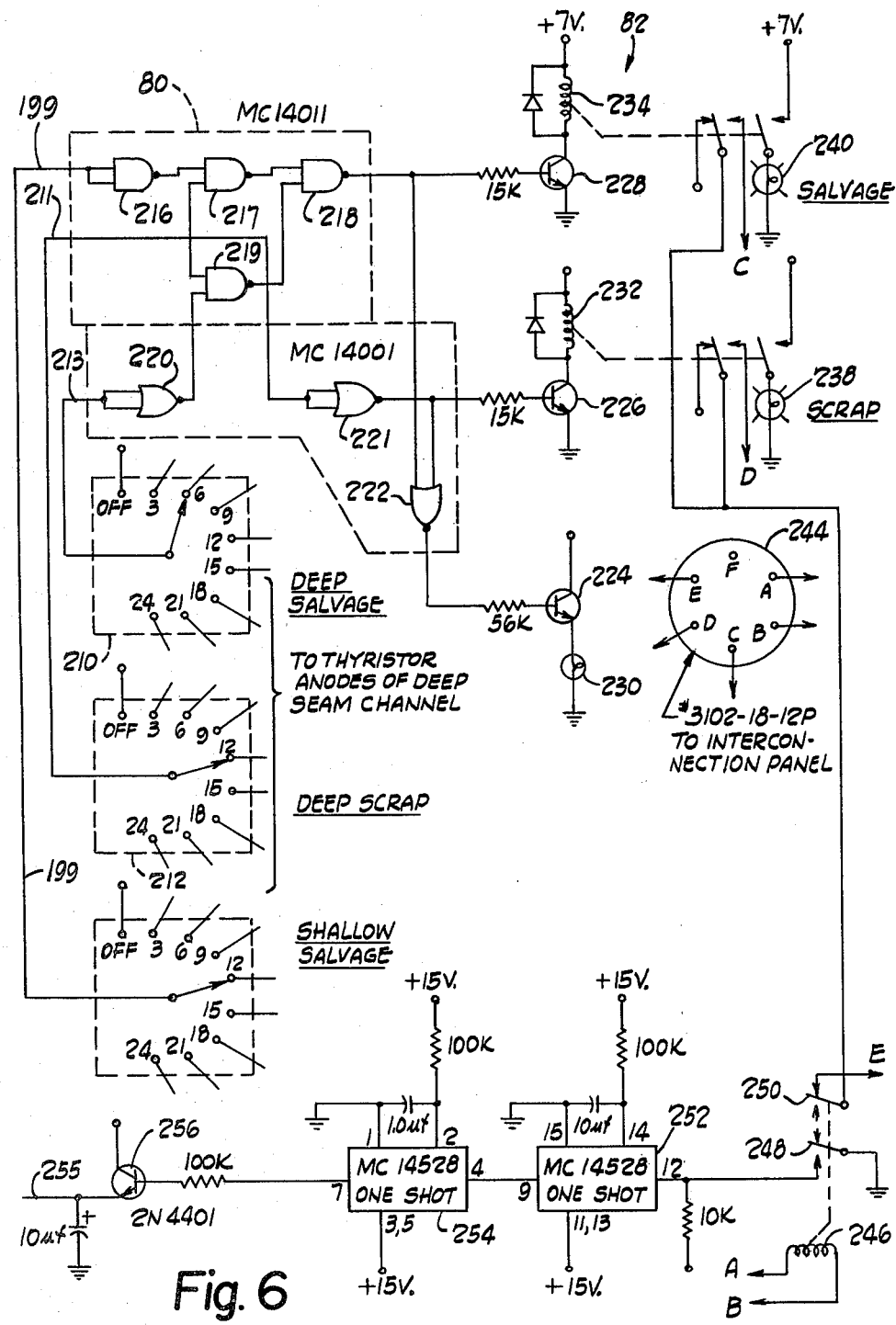

The deep seam channel in the flaw classification circuit 72 has two switches 210, 212 (FIG. 6) similar to a multiposition switch 198 in the shallow seam channel. These two switches 210, 212 allow deep seams in the workpiece to be classified according to length in a manner identical to the operation of the switch 198 in the shallow seam channel. A first of the deep seam switches 210 is labeled a salvage switch in FIG. 6 and typically contacts an output from LED's in the deep seam channel corresponding to a relatively short deep seam flaw along the length of the workpiece. In FIG. 6, the deep salvage switch 210 has been coupled to the 6 inch deep flaw output. The second of the two switches 212 has been labeled a deep scrap switch and typically is coupled to a LED in the deep seam channel corresponding to a longer deep seam in the workpiece. In the embodiment illustrated, the deep seam scrap switch 212 has been coupled to the 12 inch LED indicator.

The workpiece classify circuit 80 (FIG. 6) classifies the workpiece according to the length and severity of the workpiece seams or defects. The circuit 80 has three inputs 199, 211, 213 from the three multiposition switches 198, 210, 212. The circuit 80 samples these three inputs and categorizes the workpiece as either good, salvage, or scrap. As the name indicates, a good workpiece is one that has either no defects or defects short enough to avoid initiating a change in output from the three multiposition switches 198, 210, 212. Salvage workpieces are those that have defects but which have no deep defect long enough to trigger an output from the deep scrap switch 212. Scrap workpieces are those workpieces in which the deep seams or defects are long enough to trigger an output from the deep scrap switch 212.

The workpiece classify circuit 80 includes a plurality of NAND gates 216–219 and plurality of Nor gates 220–222 to implement the criteria described. In logic format this circuitry causes the workpiece to be classified according to the following logic equations:

Good = $\overline{A}.\overline{B}.\overline{C}$
Salvage = $A.\overline{C} + B.\overline{C}$
Scrap = $C$ Where A = shallow salvage output, B = deep salvage output and C = deep scrap output.

The workpiece classify circuit 80 is coupled to three transistors 224, 226, 228. A high input to the base of these three transistors causes them to conduct current. It should be appreciated to those skilled in the art that so long as the output from all three switches 198, 210, 212 is high, the first of the transistors 224, will conduct and a good indicator light 230 will indicate the workpiece under examination is good. In a similar manner, the other two power transistors 226, 288 will be turned on at an appropriate time when the workpiece is either salvageable or scrap. The second transistor 226 corresponds to the scrap indication and the third transistor 228 passes current when the workpiece is a salvageable piece.

Energization of either of the second two transistors 226, 228 means the workpiece is not "good" and must be separated from the remaining workpieces that have passed through the inspection station. To implement this step, the two transistors 226, 228 are coupled to two relays 232, 234. Energization of the first relay 232 by the transistor 226 closes a contact causing a scrap indicator 238 to light. In a similar manner energization of the second power transistor 228 energizes a second relay 234 thereby energizing a salvage indicator light 240.

Energization of the two relays 232, 234 in addition to energizing the scrap and salvage indicator lights 238, 240 completes an interconnection to an interconnection panel 244. When the first relay 232 (scrap relay) is energized pins D and E on the panel 244 are connected. When the second relay 234 (salvage relay) is energized points C and E are connected. This panel 244 is in turn coupled to circuitry for routing the workpiece after it has passed by the inspection station 10 into a storage area for either salvageable, or scrap workpieces. If the workpiece is good no re-routing procedure is required. Mechanisms and circuitry for this purpose are known in the art and therefore have not been disclosed in the present description. The earlier referenced '809 patent to Republic Steel, for example, discloses a mechanism for routing the workpieces in response to control signals from the routing circuit 80.

Once the workpiece has left the inspection station it is necessary that the thyristors 180–187 be turned off so that subsequent workpieces may be analyzed and classified. It should be appreciated that in addition to the thyristors 180–187 comprising a portion of the shallow seam channel, there are a plurality of thyristors in the deep seam channel which are also reset once the workpiece has exited from the inspection station. As the workpiece exits the inspection station a switch (not shown) coupled to contact pins A and B on interconnection panel 244 is closed thereby energizing a relay 246 shown at the bottom of FIG. 6. Energization of this relay 246 closes one associated contact 248 and opens a second associated contact 250. Closure of the first contact 248 causes a 500 millisecond output from a one shot 252 which in turn causes a 50 millisecond output from a second one shot 254. The second one shot turns on a transistor 256 which has its emitter coupled to the anodes of each of the light emitting diodes 190–197 via an interconnection 255. When the transistor 256 conducts these anodes receive a low voltage input thereby turning off the LED's. This effectively resets the thyristor/LED pair and enables the shallow seam channel to be reset to analyze subsequent workpieces at the workpiece station. It should be appreciated that although not shown a similar interconnection exists for resetting corresponding LED's and thyristors in the deep seam analysis channel. The opening of the second contact 250 disables the routing mechanism (not shown) by opening the path to pin E from either pin C or pin D on the interconnection panel 244.

Figure 7:
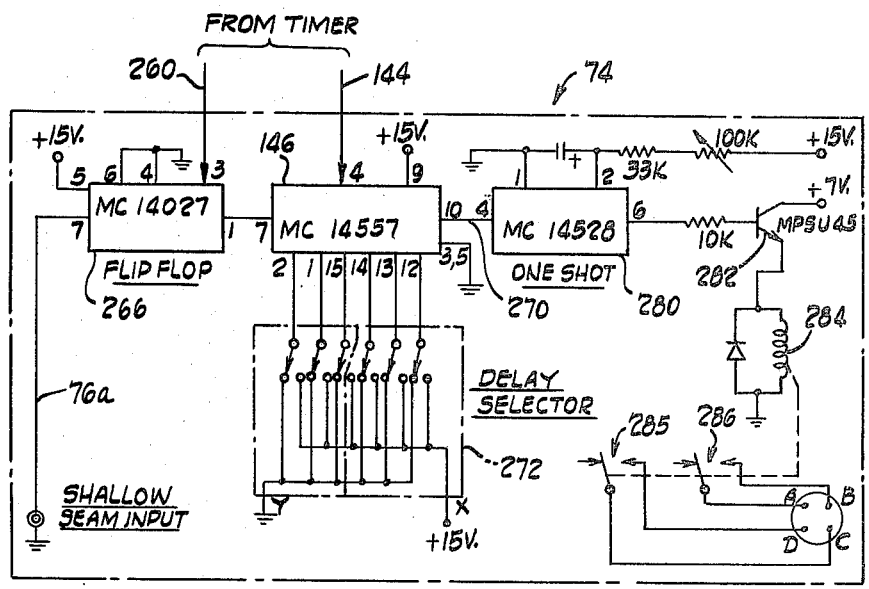
FIGS. 4-7 are more detailed schematics of the control circuitry shown generally in FIG. 3.

As the defect classifying circuitry 72 is classifying each flaw detected by the probe the timing control circuit 70 is also controlling the operation of a marker delay circuit 74 (see FIG. 7). Since the exemplary inspection technique uses four probes and four markers there are four marker delay circuits identical to the marker delay circuit 74 shown in FIG. 7. The marker delay circuit 74 has three inputs 144, 260, 76a. One of the inputs 76a is coupled to one of the four shallow seam inputs. Whenever this input 76a goes high in response to the detection by the probe of either a shallow or a deep seam the input 76a causes a change in state of a flip-flop 266 in the marker control circuit 74. This change in state is stored within the flip-flop 266 until that flip-flop receives a "high" signal on a second input 260. Both this second input 260 and the third input 144 to a programmable shift register 146 come from the timing control circuit 70. The input 144 is coupled to the first frequency divider 132 and therefore comprises an oscillating signal with a frequency 64 times greater than the frequency of rotation of the workpiece. The second input 260 is also coupled to this first frequency divider but has been delayed by approximately 2 microseconds by the one shot 142 (FIG. 5).

The sequence of entering signals into the programmable shift register 146 from the probe is as follows. A defect is detected and a shallow or deep seam input appears at the flip-flop 266. This input causes the flip-flop to change states indicating that a defect has been detected. The next signal on the input 144 from the first frequency divider 132 causes a high bit to be stored in the first bit of the programmable shift register 146. The output from the first frequency divider 132 is also transmitted through the 2 microsecond one shot 142 and input to the flip-flop 266. This causes the flip-flop to again change states and await the receipt of subsequently detected flaws. As the first frequency divider generates output signals to the input 144 the defect information stored in the programmable shift register 146 is clocked through the shift register to an output 270.

The programmable shift register introduces a requisite timing delay between the receipt of a defect signal and the activation of the marker 14. The correct delay time is a function of the mechanism used to mark the defect and can vary from one system to the next. The programmable shift register 146 is a 64 bit register and therefore the maximum delay corresponds to one workpiece revolution. Since the marker mechanism takes a finite time period to bring the marker 14 in contact with the workpiece 18, however, the actual delay typically is somewhat less than the time required for one workpiece rotation. The programmable shift register 146 is coupled to a delay selector switch 272 by a series of six inputs. By properly programming the delay selector switch 272, it is possible to introduce a delay of anywhere from 1 to 64 clock pulses between the introduction of a "high" defect signal at pin 7 of the shift register 146 to the output of that "high" signal on pin 10.

The appearance of a high output from the programmable shift register 146 at the output 270 causes a one shot 280 in turn on a transistor 282. The turned on transistor energizes a relay 284 in the delay circuit which in turn closes two contacts 285, 286. Closure of these contacts 285, 286 causes marker actuation circuitry (not shown) to cause the marker 14 to come in contact with the workpiece 18 at a location approximately coincident with the position of the detected flaw. As noted above, the application of a mark to the workpiece occurs at a position downstream of the probe 12 and in the preferred embodiment of the invention the mark is applied one rotation of the workpiece subsequent to the detection of a particular flaw.

As mentioned above, detection of a flaw on the workpiece causes the timing circuit 70 to resynchronize itself and thereby center that flaw within a workpiece quadrant. This function is performed by the introduction of an input 147 to the second frequency divider 134 each time pin 7 on the flip-flop 116 receives an input. Receipt of a shallow or deep seam flaw causes the signal at this pin to go high and changes the state of a one shot 288 causing the one shot to generate a high output 289 to the second frequency divider 134.

The second frequency divider 134 which generates the clock (CLK) and not clock ($\overline{CLK}$) signal comprises a programmable divide by N four bit counter which has been programmed to divide by 16. Receipt of the high input 289 from the one shot 288 resets the second divider 134 to a count of eight. Resetting the count to 8 centers the sensed flaw within the workpiece quadrant in which it has been detected. As the clocking pulses 143 from the first divider 132 continue, the second frequency divider 134 counts down to 0 and then outputs a clock pulse (CLK) so that the clock signal CLK appears 8 counts or one eight bar rotation after receipt of the sensed flaw.

By resynchronizing the timing function used to clock the deep and shallow channel shift registers the accuracy of flaw length determination is maintained even though the drive roller 16 used to rotate the workpiece past the probe may vary slightly in its operation. It is possible, for example, that even though the thumbwheel switches have been properly adjusted for the particular diameter bar the roller 16 may slip and thereby produce a slight missynchronization between the timing circuit 70 and the speed of rotation of the workpiece. Such a missynchronization is corrected for each time a defect is detected by the resynchronization input 147 to the second frequency divider.

A second divide by N counter 290 is coupled to the synchronization one shot 288 and resets that one shot after one complete bar revolution. A high output 289 from the one shot 288 sets this programmed counter 290 to a count of four. Since the counter 290 is coupled to the clock (CLK) output from the second divider 134 the counter 290 changes counts once every quarter of bar rotation. When the counter 290 counts down to zero its output 291 goes high resetting the one shot 288 thereby enabling it for resynchronization of the clock (CLK) pulses on subsequent bar revolutions past the probes.

While the preferred embodiment of the invention has been described with a degree of particularity it should be appreciated that certain modifications can be made. For example, rather than 64 clock pulses per workpiece revolution it is possible that some other standard frequency could be adopted and adjustments made in the digital circuitry to compensate for such adjustment. Rather than four quadrants the workpiece could be conveniently divided into some other integer number of segments to more accurately scan for flaws and defects. An exemplary technique for rotating the workpiece has been illustrated in FIGS. 1 and 2 and other mechanisms are known in the art for scanning probes in relation to rotating workpieces. The present circuitry would function equally well should the probe be rotated and translated past a stationary workpiece along a helical path. The technique for classifying the workpiece is also subject to change. The criteria for determining a "good", "salvageable", and "scrap" workpiece might be altered and indeed will be altered as the performance criteria of the bar is changed. From the above it should be apparent that certain modification could be made in the scanning of workpieces without departing from the spirit or scope of the invention as defined in the appended claims.

I claim:

1. In a workpiece classifying and marking system including a test head for generating defect signals from a workpiece which both rotates and traverses past said test head, an improved timing control circuitry comprising:
    (a) a single pulse generator for generating a series of regularly occurring pulses;
    (b) means for receiving said regularly occurring pulses and producing a first series of output pulses with an adjustable frequency related to the speed of workpiece rotation and coupled to a workpiece marking control to coordinate workpiece marking with rotation; and
    (c) divider means coupled to the first series of output pulses for generating a second series of output pulses with a frequency greater than the frequency of workpiece rotation and coupled to a classifying circuit to coordinate workpiece classification and workpiece rotation by categorizing the defect signals according to the position of the defect around the pipe circumference.

2. A method for classifying workpiece defects according to length comprising the steps of:
    (a) rotating and translating a workpiece past a probe which detects the presence of a defect by producing a signal output;
    (b) generating a series of pulses from a single generating source with a repetition frequency four times the frequency of rotation of said workpiece, said workpiece thus being divided into four quadrants;
    (c) storing signal outputs from said probe in a serial storage means;
    (d) coupling the storage means to the series of pulses to clock the outputs through the storage means at a rate equal to the repetition frequencing;
    (e) sensing the condition of said storage means to correlate said condition to the length of a sensed defect; and
    (f) resynchronizing the clocking of said storage means when a defect is sensed to position said defect approximately in the center of said quadrant.

3. In a workpiece classifying and marking system including a test head for generating defect signals from a workpiece which both rotates and traverses past said test head a control circuit comprising:
  (a) signal analysis means for receiving defect signals and analyzing them according to defect severity having first and second outputs for transmitting shallow and severe defect signals respectively;
  (b) marker control means connected to the signal analysis means for energizing a workpiece marker in response to the receipt of both shallow and severe defect signals by said signal analysis means and including defect signal delay means for delaying energization of the marker until the workpiece has completed at least one revolution from the orientation where the defect corresponding to the defect signal was detected;
  (c) workpiece classifying means including a shallow defect signal and severe defect signal receiving channel for storing said defect signals; each of said channels including sequential storage means for storing an indication of the defect signals in serial fashion as the workpiece moves past the test head; said classifying means further including logic circuitry coupled to the sequential storage means to determine the length of the shallow and severe defects; and
  (d) a single timing means for controlling the delay in said delay means, dividing the workpiece rotation into four quadrants and controlling the transmittal of defect signals through the sequential storage means by clocking the sequential storage means with a clocking signal; said timing means including resynchronization means for resynchronizing the clocking signal when a defect is sensed by the test head to locate said defect approximately at the center of a quadrant.

* * * * *